United States Patent [19]

Hanotier et al.

[11] 4,334,086

[45] Jun. 8, 1982

[54] PRODUCTION OF TEREPHTHALIC ACID

[75] Inventors: Jacques D. V. Hanotier; Monique J. S. Hanotier-Bridoux, both of Lasne Chapelle St. Lambert, Belgium

[73] Assignee: Labofina S.A., Brussels, Belgium

[21] Appl. No.: 244,141

[22] Filed: Mar. 16, 1981

[51] Int. Cl.$^3$ ............................................. C07C 51/16
[52] U.S. Cl. ................................................... 562/413
[58] Field of Search ........................................ 562/413

[56] References Cited

U.S. PATENT DOCUMENTS 2,962,361  11/1960  Spiller et al. ...................... 562/413

FOREIGN PATENT DOCUMENTS 1583755  2/1981  United Kingdom ................ 562/413

Primary Examiner—Alan Siegel

[57] ABSTRACT

Disclosed is a process for the continuous production of terephthalic acid from p-xylene, comprising the steps of oxidizing p-xylene in a first oxidation zone in the presence of not more than about 10 weight % of water and a cobalt/manganese catalyst up to a conversion of about 15% terephthalic acid; oxidizing the partially-oxidized compounds in a second oxidation zone in the presence of an additional amount of water up to about 20 to 70% by weight and in the presence of an additional amount of the catalyst up to a conversion of about 50% by weight terephthalic acid; stripping p-xylene vapors from the second oxidation zone; separating crystals of crude terephthalic acid from the effluent from the second oxidation zone from the soluble components of the effluent; countercurrently washing the separated crystals with fresh water to produce a slurry; recycling a part of soluble components to the second oxidation zone, and another part of the first oxidation zone to provide the latter with heavy metal catalyst; and recovering purified terephthalic acid by recyrstallizing the crystals contained in the slurry.

9 Claims, 1 Drawing Figure

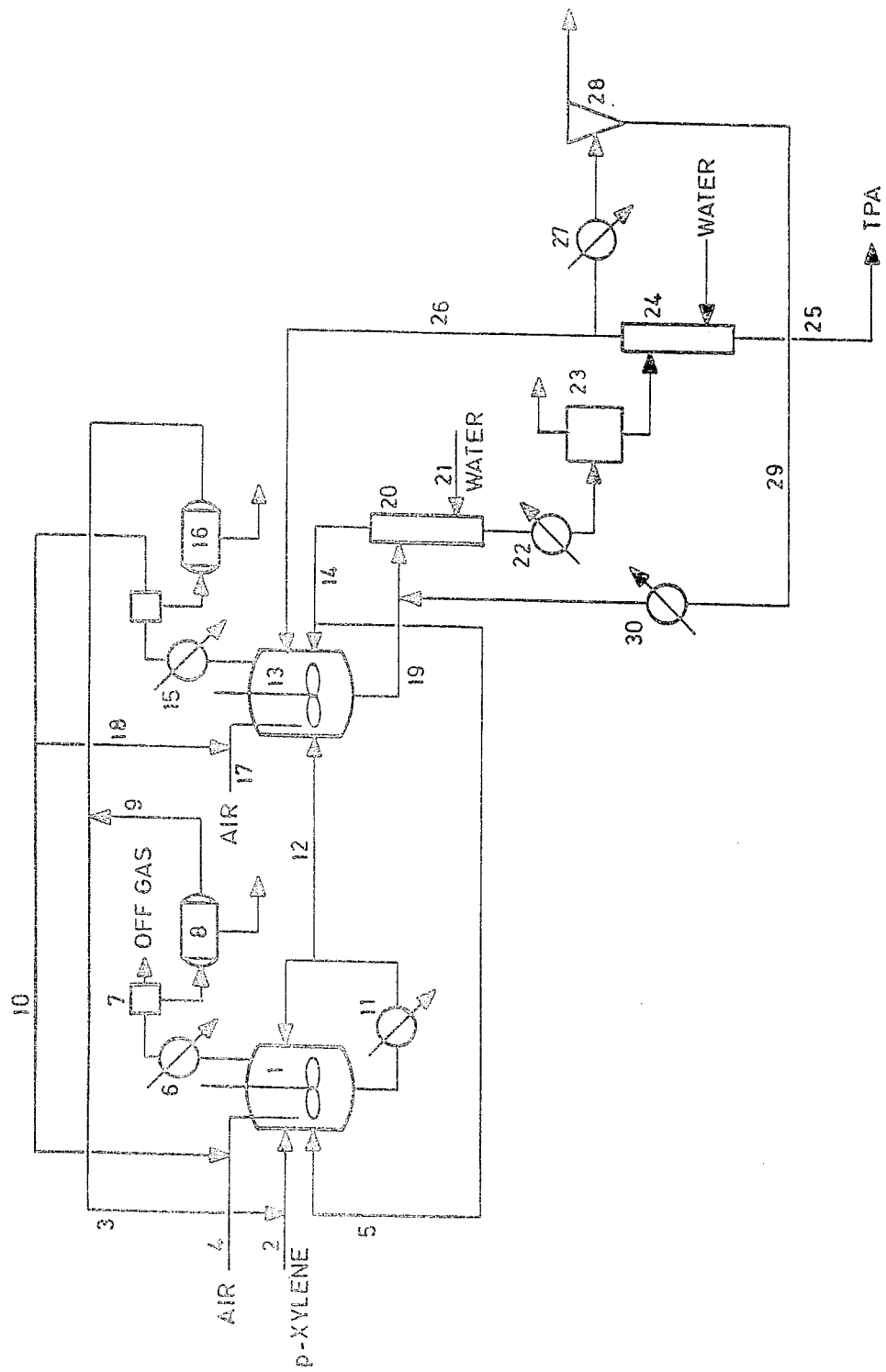

PRODUCTION OF TEREPHTHALIC ACID

BACKGROUND OF THE INVENTION

The present invention relates to the production of terephthalic acid, and more especially, to the production, in high yield, of good quality terephthalic acid by liquid-phase oxidation of p-xylene in a continuous multi-stage process, without resorting to the use of an extraneous carboxylic acid diluent, and by recrystallization of the resulting crude terephthalic acid at high temperature.

One major problem in the manufacture of terephthalic acid by oxidation of any precursor, e.g., p-xylene, p-toluic acid and/or p-tolualdehyde, results from the fact that terephthalic acid is an insoluble and infusible solid under most practical conditions. The handling thereof and its separation from the other components of the reaction mixture therefore requires the use of a suspension medium. Typically, acetic acid is used for this purpose. For instance, in U.S. Pat. No. 3,064,044, there is described a two-stage process wherein p-xylene is primarily oxidized at relatively low temperature, i.e., in the range of 150° to 205° C., in the presence of a heavy metal catalyst, a source of bromine and aqueous acetic acid as a diluent. Partially oxidized compounds from the first oxidation state are then oxidized into terephthalic acid at higher temperature, i.e., 185° to 225° C., under substantially anhydrous conditions. Terephthalic acid of improved quality is obtained by this process in comparison with previous methods wherein the oxidation of p-xylene into terephthalic acid is carried out in one stage.

However, as explained in British Pat. No. 1,555,246, "the foregoing concept for the use of a combination of primary and secondary oxidations has the undesirable effect of more than doubling the burning of acetic acid solvent which would occur in a single oxidation zone because of the higher temperature of operation in the secondary oxidation using substantially anhydrous acetic acid solvent and using in the secondary oxidation concentrations of catalyst components suitable for the lower temperature operation in the primary oxidation zone but unsuitable for the higher temperature oxidation. The increase in acetic acid burning is due to the increase of secondary oxidation operating temperature, metal oxidation catalyst concentration, residence time, and decrease in water content of acetic acid solvent". (page 1, lines 40–45, and page 2, lines 1–3).

To avoid the problems associated with the use of acetic acid as a suspension medium for terephthalic acid, a two-stage process has been proposed in U.S. Pat. No. 3,406,196, which comprises oxidizing p-xylene in a first stage until the major part thereof is transformed into partially-oxidized compounds, with this oxidation being carried out at a relatively low temperature, particularly 155°–175° C., in the absence of acetic acid and preferably in the presence of not more than 10% by weight of water, with a heavy metal as catalyst and a source of bromine. The resulting oxidation products are then oxidized in a second stage at high temperature, particularly 225° to 250° C., in the presence of added water to maintain a workable slurry as the partially-oxidizing compounds from the first stage are transformed into terephthalic acid. Under such conditions, "overall polycarboxylic acid yields, based on polyalkyl aromatic starting compound, on the order of 85% and generally 90% or higher have been demonstrated". (column 9, lines 72–75)

Although the problems associated with the use of acetic acid are indeed eliminated when operating in accordance with the teachings of this last patent, certain other difficulties remain which make the process difficult to apply in practice. For instance, the high temperatures used in the second stage combined with the presence of water, a bromine compound such as hydrogen bromide and the light organic acid necessarily present in the system as degradation products result in tremendous corrosion problems. When, in an attempt to alleviate these corrosion problems, the bromine compound is omitted, degradation and other side reactions of the partially-oxidized compounds become so important at the high temperatures used in the second stage that the terephthalic acid produced is heavily colored, and the overall yield thereof based on p-xylene consumed becomes unacceptably low.

Another difficulty with this two-stage process relates to the recovery and recycle of the heavy metal catalyst, especially when the process is to be carried out in a continuous manner. According to that patent, passing from the first to the second stage of oxidation involves increasing the temperature sufficiently, with additional water being added in the course of this second stage. Reaction is then continued until oxygen absorption has ceased. The reaction mixture is then cooled and terephthalic acid crystals are filtered and washed with water. Obviously, the heavy metal catalyst remains dissolved in the aqueous mother liquor, with the practical consequence that, for recovering this catalyst, large amounts of water must be removed, e.g., by distillation, which would add significantly to the cost of producing the terephthalic acid.

Recently, in U.S. patent application Ser. No. 30,054, a process has been disclosed for the oxidation of p-xylene wherein water is used as a substitute for acetic acid. Thus, the difficulties experienced with most other methods as related to the burning, handling and recovery of acetic acid are, here also, completely avoided. In carrying out this new process, p-xylene is fed into the oxidation zone which contains, in addition to unreacted p-xylene, partially-oxidized oxidation products, terephthalic acid, a heavy metal catalyst, i.e., cobalt and/or manganese in proper amounts, and water as a diluent. No bromine compound is used and, in addition, because the temperature applied is relatively mild, no serious corrosion problems arise so that conventional materials, such as stainless steel can be used for the reactor and the other parts of equipment. As taught in U.S. patent application Ser. No. 186,101, terephthalic acid produced in the reaction can be continuously separated by gravity in a sedimentation column, wherein it is washed counter-currently with fresh water injected near the bottom of said column. The washing liquors recovered from the top of the column are at least for the main part introduced into the oxidation zone to compensate for the water stripped therefrom as vapors by the air flow. When the column is properly operated, that liquor contains all of the soluble components present in the reactor effluent, including the heavy metal catalyst, which is therefore automatically recycled.

However, in practicing this method, special care must be taken to avoid increasing the water concentration in either the oxidation zone or in the sedimentation column up to such a point that an organic phase rich in unreacted p-xylene would separate. In the oxidation zone, such a phase separation would bring about technical problems associated with homogenization, oxygen dispersion and mass-transfer effects. Complete deactivation of the catalyst may even take place through extraction thereof into the aqueous phase, with the result that the oxidation reaction would suddenly break down. If, on the other hand, phase separation should take place in the sedimentation column, terephthalic acid could not be separated efficiently from the water-soluble components of the reaction mixture.

To prevent those difficulties, it has been recommended to work at sufficiently high temperatures, depending on the amount of water and unreacted p-xylene present in the system. Actually, when a relatively high water content, e.g., 30 to 60% by weight, is desired for taking full practical advantage of the use of water as a diluent and for minimizing the amount of partially-oxidized products occluded as impurities in the terephthalic acid crystals, a temperature of 180° to 200° C. is preferably applied, combined with a relatively high concentration of catalyst. Under such conditions, the oxidation of p-toluic acid, which is the major oxidation intermediate from p-xylene, takes place smoothly with high yields and practical rates. However, it has been found that with p-xylene present under the same conditions, appreciable degradation takes place, with the consequence that the overall yield of terephthalic acid based on p-xylene becomes unacceptably low.

SUMMARY OF THE INVENTION

It is therefore an object of the present invention to provide an improved process for the production of therephthalic acid.

A further object of the invention is to provide an improved process for the continuous production of good quality terephthalic acid in aqueous medium.

It is a more specific object of this invention to provide such a process wherein terephthalic acid is obtained in high yield from p-xylene by oxidation with molecular oxygen.

Still a further object of this invention resides in achieving this oxidation under mild conditions, without resorting to the use of any brominated activator.

According to the present invention, there is provided an improved process for the continuous production of terephthalic acid from p-xylene which comprises the following steps:

(a) oxidizing p-xylene in a first oxidation zone at a temperature comprised between about 130° and 170° C. in the presence of not more than about 10% by weight of water and a mixture of cobalt and manganese salts as catalyst, the residence time in this first oxidation zone being such that not more than about 15% by weight of the equilibrium reaction mixture is comprised of terephthalic acid;

(b) oxidizing the partially-oxidized compounds formed in the first oxidation zone in a second oxidation zone in the presence of additional water up to a concentration of from about 20 to 70% by weight of liquid phase and an additional amount of the same catalyst as used in said first oxidation zone, at a temperature of from about 180° to 200° C. and at a pressure high enough to maintain an oxygen partial pressure of at least about 0.05 kg/cm$^2$, the residence time in the second oxidation zone being such that not more than about 50% by weight of the equilibrium reaction mixture is comprised of terephthalic acid, and wherein p-xylene stripped as vapor from this second oxidation zone is recycled to the first oxidation zone;

(c) transferring the effluent from the second oxidation zone into a first sedimentation column wherein crystals of crude terephthalic acid are separated by gravity from the soluble components of the effluent and washed countercurrently with fresh water introduced near the bottom of the column;

(d) recycling the soluble components to the second oxidation zone, a part thereof comprised between about 2 and 20% being diverted to the first oxidation zone to provide the latter with enough heavy metal catalyst;

(e) heating the slurry of crude terephthalic acid crystals recovered from the bottom of the first sedimentation column up to a temperature at least about 5° C. higher than necessary for having the resulting solution saturated with terephthalic acid;

(f) transferring the resulting solution of crude terephthalic acid into a crystallization zone where it is cooled down to a temperature not lower than about 185° C., whereby purified terephthalic acid crystals separate; (g) transferring the resulting slurry of purified terephthalic acid into a second sedimentation column operated at a temperature not lower than the final temperature of crystallization, wherein purified terephthalic acid crystals are separated by gravity from their mother liquor, washed countercurrently with fresh water and recovered from the bottom of the column; and (h) recovering and recycling to the second oxidation zone the dissolved material present in the water solution recovered from the top of the second sedimentation column.

Further objects, features and advantages of the present invention will become apparent from the detailed description of preferred embodiments which follows, when considered together with the attached FIGURE of drawing.

BRIEF DESCRIPTION OF THE DRAWING

The FIGURE of drawing is a schematic flow sheet illustrating one embodiment for carrying out the process according to the present invention.

DETAILED DESCRIPTION OF PREFERRED EMBODIMENTS

It is a well known fact that p-toluic acid can easily be obtained by oxidation of p-xylene with molecular oxygen in the presence of a heavy metal catalyst. However, p-toluic acid itself is relatively inert under the same conditions and cannot be transformed easily into terephthalic acid unless high temperatures and some radical source is used as a promoter. The most common promoter used for this purpose is bromine or a bromine-containing compound. For instance, in U.S. Pat. No. 2,907,792 there is described a method whereby p-toluic acid can be oxidized in good yields into terephthalic acid by oxidation at a high temperature, e.g., 200° C., in an aqueous medium in the presence of hydrogen bromide. Under the same conditions, however, the oxidation of p-xylene into useful oxygenated derivative, i.e., p-toluic acid and/or terephthalic acid, takes place with very low yields. As taught in U.S. Pat. No. 3,406,196, already cited, similar results are obtained at still higher temperatures, e.g., 225° to 250° C. The role of bromine in these methods is essential; it has been observed that, when it is omitted, the oxidation of p-toluic acid at such high temperatures takes place at much reduced rates and yields in spite of the presence of cobalt and manganese salts as catalysts. Moreover, when the reaction is speeded up by increasing the concentration of catalyst, still lower rates and yields are obtained.

The process of the present invention is based in part on the observation that, surprisingly, at temperatures below about 200° C. the situation is completely reversed, i.e., the oxidation of p-toluic acid in an aqueous medium only takes place in the presence of relatively high concentrations of catalyst, and when this condition is satisfied, the rate of the reaction is not improved and may even be reduced by the presence of bromine. In other words, it has now been possible to produce terephthalic acid from p-toluic acid under much milder conditions than could be anticipated based upon the knowledge in the prior art.

The temperature to be used for the oxidation of p-toluic acid into terephthalic acid has to be chosen based on consideration of different factors. In any case, it will be high enough for having p-toluic acid completely dissolved in the amount of water added as the suspension medium for terephthalic acid. This is determined by the phase diagram for mixtures of water and p-toluic acid. Thus, from the date provided by Sidgwick et al. (J. Chem. Soc. 107, 1202, 1915), it can be seen that when the water concentration is 25–30% by weight, temperatures as low as 145°–150° C. can be used. On the other hand, when it is 60–65%, a temperature of higher than 160° C. is necessary for having both components forming a homogeneous solution. In most practical cases, however, a temperature of between about 180° and 200° C. will be selected for ensuring active oxidation and therefore high reaction rates, especially when relatively high amounts of water are present in the reaction mixture. As an illustration, it has been determined that in the presence of, e.g., 25% by weight of water and with a manganese to cobalt ratio of 1:1 in the catalyst, the specific rate of formation of terephthalic acid from p-toluic acid increases from 0.032 hour$^{-1}$ at 150° C. to 0.366 at 190° C., that is, about a tenfold increase, whereas in the same time the molar yield in terephthalic acid decreases only from 95 to 93 mole %.

The amount of water to be added as the diluent is likewise not critical. Obviously, the more diluted the system is, the higher will be the purity of the terephthalic acid crystals formed therein, but this advantage may be counterbalanced by the fact that the specific rate of oxidation of p-toluic acid decreases significantly as the dilution with water increases. In most cases, the concentration of water in the liquid phase where p-toluic acid is being oxidized, will advantageously be comprised between about 20 and 70% by weight, still more advantageously between about 35 and 55%.

The minimum concentration of catalyst to be used for the oxidation of p-toluic acid in such aqueous media has been specified in the U.S. patent application Ser. No. 68,648. It is independent of temperature but depends on the proportion of manganese and cobalt in the catalyst and on the water-to-p-toluic acid molar ratio in the reaction mixture at equilibrium. For instance, in a reaction mixture comprising 65 parts by weight of water for 35 parts of p-toluic acid, the water-to-p-toluic acid molar ratio is 14, and the minimum concentration of catalyst to be used when manganese and cobalt are in equimolar amount is about 6–8 mmoles per kg of liquid phase. Below this value, no reaction will take place at all. This concentration, however, will not ensure a high reaction rate. As a matter of fact, it has been observed that, above this minimum concentration, the reaction rate and yield of terephthalic acid increase with catalyst concentration up to a plateau which, in the case considered above, is reached for a concentration of metal catalyst of about 20 mmoles per kg of liquid phase.

On the other hand, in a reaction mixture comprising only 25 parts by weight of water for 75 parts of p-toluic acid, the water-to-p-toluic acid molar ratio is 2.5, and in this case, the minimum concentration of metal catalyst to ensure oxidation with the same equimolar mixture of manganese and cobalt is 3.2 mmoles per kg of liquid phase, i.e., about one half of that in the previous case. But again, it is observed that the maximum rate and yield are obtained for a higher value, actually about 10 mmoles per kg. Thus, it can be seen that, in most practical cases, the concentration of metal catalyst will be comprised between about 5 and 30 mmoles of heavy metal compound per kg of liquid phase wherein the oxidation reaction is taking place.

The oxidizing agent used for oxidizing p-toluic acid in aqueous medium in accordance with the present invention is preferably molecular oxygen, either in pure form or diluted with inert gases, as in air. For obvious economic and safety reasons, air is preferred and for the same reasons it will be provided at such a flow rate as to have less than about 8% by volume of oxygen in the off-gas, calculated on a vapor-free base. To ensure active oxidation, provision should be made for efficient contact between the liquid reaction mixture and the oxidizing gas phase. Nevertheless, even when the oxygen-containing gas is efficiently dispersed, unsatisfactory results may be obtained with respect to reaction rate and product purity if the oxygen partial pressure in the gas phase is too low. It is known that oxygen starvation may result in free-radical coupling and other undesired side reactions. In most cases, oxygen partial pressures higher than about 0.05 kg/cm$^2$ will be sufficient to avoid or to limit substantially the occurrence of such side reactions. However, for ensuring maximum reaction rates, oxygen partial pressures of at least about 0.7 should be applied. For each particular case, the skilled worker will easily determine the balance between the effects of the air flow rate and of total pressure in order to take the maximum advantage of both.

When it is desired, as in the present process, to use p-xylene as a raw material for the manufacture of terephthalic acid, it is obviously possible to add progressively p-xylene into the aqueous system where p-toluic acid is being oxidized, at such a rate as to compensate by in situ formation of p-toluic acid the amount thereof which is consumed by the reaction. However, and this is another observation on which the present invention is based, in spite of the mild conditions used in this process to oxidize p-toluic acid as compared with the prior art, the oxidation of p-xylene under the same conditions takes place with extensive degradation thereof, especially when the temperature is higher than 180° C., with the consequence that the resulting gain in reaction rate is at least partly cancelled by a significant loss in terephthalic acid yield. For instance, it has been determined that, in the presence of, e.g., 25% by weight of water and with a manganese to cobalt ratio of 1:1 in the catalyst, the molar yield of p-toluic acid from p-xylene decreases from 99% at 150° C. to only 89% at 190° C.

To obviate this difficulty, p-toluic acid to be oxidized into terephthalic acid is not produced in situ but, in accordance with the present invention, is produced in a separate oxidation zone operated under more appropriate conditions. As apparent from the foregoing, these conditions comprise operating at the lowest temperatures still compatible with practical rates for p-toluic acid production. In most cases, these temperatures will be comprised between about 130° and 170° C., preferably between about 140° and 160° C. Water is not detrimental in this reaction; however, it should not be present in such an amount as to cause phase separation, for in this case the catalyst might be extracted from the organic phase into the aqueous phase, with the consequence that no reaction would be possible any longer in the former. To avoid such a possibility, the concentration of water in the reaction mixture where the oxidation of p-xylene is taking place should be maintained below about 10% by weight, depending on temperature, and preferably below about 5%. Under such relatively anhydrous conditions, the concentration of catalyst to be used for ensuring reaction can be substantially lowered. In most cases, it will be comprised between about 1 and 10 mmoles of metal compound per kg of liquid phase.

The catalyst used in the process of the present invention is a salt of cobalt and/or manganese which is soluble in the reaction mixture under the reaction conditions. Salts of lower aliphatic carboxylic acids are generally used, and more particularly the acetates.

The invention will now be further described with reference to the flow-sheet shown in the accompanying drawing, which illustrates one particular way to practice in continuous operation the oxidation of p-xylene into terephthalic acid via p-toluic acid as a major intermediate compound, and also one embodiment of the terephthalic acid recovery and purification systems which is another feature of the present invention. Referring to the drawing, p-xylene to be oxidized is charged into a first oxidation zone or oxidizer 1 through line 2 wherein it is mixed with p-xylene recycled from line 3 as explained hereinafter. Air is admitted into the same oxidizer through line 4, and the heavy metal catalyst is introduced through line 5 as part of the water solution recovered from the separation of terephthalic acid as explained hereinafter. Vapors of p-xylene and water stripped by the air flow through oxidizer 1 are condensed in heat exchanger 6 and separated from the off-gas in gas-liquid separator 7. The resulting condensate comprises two liquid phases which are separated in decanter 8. The hydrocarbon phase, which consists essentially of p-xylene, is recycled to oxidizer 1 via lines 9 and 3, whereas the aqueous phase, which consists of a water solution of low molecular weight degradation products, e.g., acetic acid and formic acid, is discarded. To help removing water from oxidizer 1 as well as the heat of reaction evolved therein, a part of the off-gas from either oxidation stage can be recycled and mixed in line 4 with fresh incoming air. For instance, advantage can be taken of the higher pressure generally required for the second oxidation stage to recycle the off-gas therefrom through line 10, as shown in the drawing. Off-gas from oxidizer 1 can also be partly recycled into oxidizer 1 to maintain the desired temperature therein through vaporization of p-xylene, but another means to achieve temperature control is to force the reaction mixture to circulate through a cooling loop, via heat exchanger 11 as shown in the drawing.

For practical reasons, it is advantageous to have the residence time in oxidizer 1 adjusted so as to have the p-xylene feed transformed mainly into partially-oxidized compounds, with relatively little formation of terephthalic acid. In most practical cases, the concentration of the latter in the reaction mixture of oxidizer 1 will be maintained below about 15% by weight. This reaction mixture is withdrawn through line 12 and transferred into the second-stage oxidizer 13, where it is diluted with enough water from line 14 to have a workable slurry of terephthalic acid in a water solution comprising the intermediate oxidation product and the catalysts. In practice, the residence time in oxidizer 13 will be selected so as to have not more than about 50% by weight of terephthalic acid in the reaction mixture present therein. Untransformed p-xylene present in line 12 from oxidizer 1 can be separated by any known means from the oxidizing component which is to be transferred into oxidizer 13. This separation can be achieved, e.g., by distillation or by solid-liquid separation after precipitation of those oxidized components by cooling. A preferred method, however, is to take advantage of the heat of reaction evolved in oxidizer 13 to evaporate p-xylene therefrom as an azeotrope with water. This azeotrope is condensed in heat exchanger 15 and both liquid phases thus formed are separated in decanter 16. The p-xylene layer is recycled into oxidizer 1 through line 3, as explained hereinabove, whereas the water layer is at least partly discarded as a purge to remove from the system the light degradation products formed in the reaction, especially light carboxylic acids, i.e., acetic acid and formic acid. Temperature control in oxidizer 13 is ensured by controlled evaporation of water. This is realized by admitting enough gas therein by mixing in line 17 with incoming fresh air a part of the off-gas recycled through line 18, while the remaining part is directed through lines 10 and 4 into oxidizer 1, as explained above.

The reaction mixture from oxidizer 13 is transferred through line 19 into sedimentation column 20 wherein impure terephthalic acid crystals are separated by gravity from the soluble components of this reaction mixture and washed countercurrently with fresh water introducing near the bottom of the column through line 21. Those soluble components are recovered from the top of the sedimentation column as an aqueous solution and recycled into oxidizer 13 through line 14, while a minor part thereof is diverted via line 5 to oxidizer 1 to provide the reaction mixture therein with enough metal catalyst. It is to be noted that the presence of high concentrations of metal catalyst in the reaction medium of oxidizer 13, which is required by the presence of relatively large quantities of water therein as compared with the reaction medium of oxidizer 1, is an especially advantageous feature for working in accordance with the process of the present invention. The amount of water solution to be diverted through line 5 can indeed be sufficiently small for having water easily stripped from oxidizer 1 without forming therein a separate aqueous phase with the undesirable consequences referred to hereinabove.

The terephthalic acid slurry from sedimentation column 20 is heated in heater 22 up to a temperature high enough for having the whole amount of terephthalic acid dissolved in water. In practice, to prevent technical difficulties which might result from premature crystallization of terephthalic acid, this heating is preferably effected up to a temperature at least about 5° C. higher than necessary for having the resulting solution saturated with terephthalic acid. This solution is then transferred into a crystallization zone schematically depicted in the drawing by vessel 23 where it is cooled, e.g., by controlled flash evaporation of water, to precipitate purified terephthalic acid crystals which are separated in sedimentation column 24 and recovered as a slurry in water from line 25.

It is an important aspect of this invention that, in order to obtain by recrystallization terephthalic acid with a purity suitable for direct polycondensation with ethylene glycol, i.e., substantially free from p-toluic acid and containing not more than, e.g., 300 to 1000 ppm of 4-carboxybenzaldehyde, it is essential that the temperature at which this recrystallization is carried out be sufficiently high, i.e., higher than about 185° C. and still preferably higher than about 200° C., and that the recovery of the precipitated terephthalic acid be effected at a temperature not lower than the one at which recrystallization has taken place. When these requirements are observed, terephthalic acid crystals of good purity can be obtained by a single recrystallization operation, without resorting to any chemical purification means, such as, hydrogenation or postoxidation, as generally is the case in the prior art. Obviously, the aqueous solution of terephthalic acid may, prior to recrystallization, be submitted to any physical treatment, e.g., with activated charcoal, without departing from the scope of the present invention.

However, the advantage resulting from carrying out the recrystallization of terephthalic acid at a high temperature in accordance with the present invention is adversely affected by the fact that, at such high temperatures, the solubility of terephthalic acid in water is relatively high. As a consequence, the effluent withdrawn through line 26 from the top of sedimentation column 24 contains not only partially-oxidized compounds, such as p-toluic acid and 4-carboxybenzaldehyde, but also contains substantial amounts of terephthalic acid, depending on the temperature at which the column is operated. In a process wherein a carboxylic acid solvent is used as a suspension medium for terephthalic acid in the oxidation reaction mixture, the recovery of the dissolved material from said effluent would require separating water, e.g., by distillation, from this material and reslurrying the latter in the carboxylic acid solvent. In the present process, since water is the common solvent for both the oxidation and purification zones, the water effluent from column 4 can at least in part be directly recycled to the oxidation zone via line 26. Another method is to cool this effluent in exchanger 27 down to a temperature at which the solubility of the material dissolved therein becomes negligible, thus bringing about the precipitation of this material, which can then be separated by any solid-liquid separation device, e.g., by hydrocyclone 28, and recycled to sedimentation column 20 via lines 29 and heater 30 as shown in the drawing.

Obviously, various modifications can be made to the illustrative procedure given hereinabove without departing from the scope of the present invention. For instance, as those skilled in the art will clearly realize, carrying out two successive recrystallizations under the specific conditions disclosed herein will result in the production of highly purified terephthalic acid which may be more suitable for certain applications.

The present invention will now be described in more detail with reference to the following examples, wherein the different operating conditions are given for the sake of illustration only and should not be considered as limiting the scope of the invention.

EXAMPLE 1

The apparatus used in this example is substantially the same as represented schematically in the accompanying drawing. Oxidizer 1 is a 316 stainless steel reactor of about 80 liters capacity into which fresh p-xylene is pumped at a rate of 100 moles, i.e., 10.6 kg per hour, through line 2. Into the same oxidizer there is pumped through line 5 an aqueous solution comprising some p-toluic acid and metal catalysts from the second oxidation stage, as explained hereinafter. The operating conditions applied to carry out the first oxidation stage are the following:

| | |
|---|---|
| Temperature | 150° C. |
| Pressure (gauge) | 20 kg/cm$^2$ |
| Air flow rate (through line 4) | 28.6 m$^3$/hour |
| O$_2$ concentration in off-gas | 7% by volume |
| Catalyst concentration (Mn/Co mole ratio: 3:1) | 3 millimoles/kg of liquid reaction medium |
| Residence time | 1.85 hours (111 min) |
| Volume of reaction mixture (non-aerated) | 52 liters (52 kg) |

The air flow rate is automatically regulated so as to maintain an oxygen content of 7% by volume in the off-gas. The residence time in oxidizer 1 is the ratio of the volume of reaction mixture in the oxidizer to the volume of said mixture withdrawn per hour through line 12. Obviously, when the flow rate of fresh feed into the oxidizer is fixed, as in the present example to 100 moles, i.e., 12.3 liters per hour, the residence time is determined by the volume of reaction mixture present in the oxidizer.

The reaction mixture from oxidizer 1 is transferred through line 12 into a second 316 stainless steel reactor, i.e., oxidizer 13 in the drawing, of about 200 liters capacity, wherein the oxidation reaction started in oxidizer 1 is continued. The operating conditions in the second-stage oxidation are the following:

| | |
|---|---|
| Temperature | 185° C. |
| Pressure (gauge) | 30 kg/cm$^2$ |
| Air flow rate (through line 17) | 23.4 m$^3$/hour |
| O$_2$ concentration in off-gas | 7% by volume |
| Catalyst concentration (Mn/Co mole ratio: 3:1) | 20 millimoles per kg of liquid reaction medium |
| Residence time | 2.20 hours (132 min) |
| Water content of the liquid reaction medium | 45% by weight |
| Volume of reaction mixture (non-aerated) | 132 liters (147 kg) |

The residence time is defined in the same way as for oxidizer 1, i.e., as the ratio of the volume of reaction mixture in oxidizer 13 to the volume of said mixture withdrawn per hour through line 19. In practice, this is determined by the rate of recycling the water-soluble components of said mixture through line 14.

Crude terephthalic acid crystals separated in sedimentation column 20 have the following composition in weight %:

| | |
|---|---|
| terephthalic acid | 93.1% |

-continued

| p-toluic acid | 4.6% |
| 4-carboxybenzaldehyde | 2.3% |

These crystals are recovered from column 20 as as a slurry in about 100 parts of water for 20 parts of terephthalic acid. This slurry is then heated in heater 22 to a temperature of 270° C. whereby the crystals present therein are brought into solution. The resulting water solution is then cooled in crystallizer 23 by controlled evaporation of water down to 220° C., whereby purified terephthalic acid crystals precipitate. These crystals are then washed in sedimentation column 24 and recovered as a slurry in pure water through line 25. Upon analysis, they are shown to contain only 700 ppm of 4-carboxybenzaldehyde.

The flow rates and composition of the different streams are given in Table 1. It can be seen that, under the conditions used, the yield of terephthalic acid produced based on p-xylene fed is 93.7 mole %. On the other hand, inasmuch as the total weight of reaction mixture in both oxidizers 1 and 13 is 52+147=199 kg, the overall productivity of the two-stage system used in this example is 0.13 kg of terephthalic acid per 100 kg of reaction mixture per minute.

EXAMPLE 2

The operation of Example 1 is repeated except that the air flow rates through oxidizers 1 and 13 are adjusted so as to reduce the oxygen content in the off-gas down to only 1% instead of 7%. No difference in the overall yield in terephthalic acid results from this modification, but since the oxygen partial pressure in both oxidizers has been lowered, the rates of reaction therein are significantly reduced. As a result, the productivity becomes 0.11 kg of terephthalic acid per 100 kg of reaction mixture per minute instead of 0.13 as in the preceding example.

EXAMPLES 3 to 7

The operation of Example 1 is repeated except that different operating variables are modified to illustrate the effect thereof on the yield and productivity in terephthalic acid. The results obtained are shown in Table 2 where, for comparison, those of Example 1 are also quoted. These data clearly show that:

(1) the yield in terephthalic acid is definitely higher as the temperature in the first oxidation state is lower, but this advantage is somewhat counterbalanced by a lower productivity (compare Examples 1, 3 and 4);

TABLE 1

| COMPONENTS | FLOW RATE (moles/hour) in apparatus bearing reference numeral (see FIGURE): | | | | | | | | | | | | |
| --- | --- | --- | --- | --- | --- | --- | --- | --- | --- | --- | --- | --- | --- |
| | 2 | 3 | 4 | 5 | 6 | 9 | 10 | 12 | 14 | 15 | 17 | 19 | 25 |
| Oxygen | — | — | 249.6 | — | 130.4 | — | 58.9 | — | — | 183.1 | 204.1 | — | — |
| Nitrogen | — | — | 939.0 | — | 1706.8 | — | 767.9 | — | — | 2388.5 | 767.9 | — | — |
| Carbon dioxide | — | — | — | — | 22.4 | — | 13.0 | — | — | 40.5 | — | — | — |
| Carbon monoxide | — | — | — | — | 3.4 | — | 1.3 | — | — | 4.2 | — | — | — |
| Acetic acid | — | — | — | 1.6 | — | — | — | 2.8 | 20.1 | 9.9 | — | 20.1 | — |
| Formic acid | — | — | — | 0.5 | — | — | — | 0.5 | 5.7 | 4.7 | — | 5.7 | — |
| Water | — | — | — | 208.2 | 323.5 | — | — | — | 2602.8 | 1246.9 | — | 1226.8 | 4319.5 |
| p-xylene | 100.0 | 114.0 | — | — | 79.1 | 79.1 | — | 114.0 | — | 114.0 | — | — | — |
| Partially-oxidized compounds (1) | — | — | — | 15.9 | — | — | — | 103.5 | 198.5 | — | — | 198.5 | — |
| Terephthalic acid | — | — | — | 0.2 | — | — | — | 10.6 | 2.8 | — | — | 96.6 | 93.7 |
| Heavy by-products | — | — | — | — | — | — | — | 0.2 | — | — | — | — | — |

TABLE 2

| EXAMPLE | Temperature (°C.) in | | Residence time (h) in[1] | | % $H_2O$ in stage 2[2] | Mn/Co in catalyst[3] | Yield %[4] | Productivity[5] |
| --- | --- | --- | --- | --- | --- | --- | --- | --- |
| | Stage 1 | Stage 2 | Stage 1 | Stage 2 | | | | |
| 1 | 150 | 185 | 1.85 | 2.20 | 45 | 3/1 | 93.7 | 0.13 |
| 3 | 130 | 185 | 1.85 | 1.20 | 45 | 3/1 | 94.6 | 0.10 |
| 4 | 170 | 185 | 0.45 | 1.80 | 45 | 3/1 | 92.1 | 0.17 |
| 5 | 150 | 185 | 1.85 | 2.30 | 65 | 1/1 | 92.1 | 0.09 |
| 6 | 150 | 185 | 1.85 | 1.10 | 25 | 1/1 | 92.1 | 0.22 |
| 7 | 150 | 195 | 2.00 | 0.40 | 25 | 1/1 | 91.8 | 0.31 |
| Comparative | — | 185 | — | 1.00 | 25 | 1/1 | 85.1 | 0.31 |

[1] The residence times in oxidizer 1 (stage 1) and 13 (stage 2) and the fraction of aqueous solution diverted to oxidizer 1 through line 5 are adjusted so as to have in each case a concentration of catalyst in oxidizer 1 of about 3 mmoles of metal compound per kg of liquid reaction medium.
[2] Weight % of water in the liquid reaction medium.
[3] Mn/Co mole ratio
[4] Molar yield of terephthalic acid based on p-xylene fed into the system.
[5] Parts by weight of terephthalic acid produced per minute per 100 parts of total reaction mixture on oxidizers 1 and 13.

(2) the yield in terephthalic acid is not affected when the concentration of water in the second oxidation stage is increased, but the productivity is severely lowered (compare Examples 5 and 6); and (3) the productivity increases markedly when temperature in the second oxidation stage is increased, but this advantage is to some extent counterbalanced by a slight decrease of the yield (compare Examples 6 and 7).

COMPARATIVE EXAMPLE

In Table 2 are also given the results obtained by performing the oxidation of p-xylene into terephthalic acid at 185° C. in a single stage. It can be seen that in this case the yield in terephthalic acid is considerably lower than in all cases where the oxidation is carried out in two stages according to the present invention.

What is claimed is:

1. A process for the continuous production of terephthalic acid from p-xylene, comprising the steps of:

(a) oxidizing p-xylene in a first oxidation zone at a temperature between about 130° and 170° C. in the presence of not more than about 10 weight % of water and a catalyst comprising a mixture of cobalt and manganese salts, the residence time in the first oxidation zone being such that not more than about 15% by weight of the equilibrium reaction is comprised of terephthalic acid;

(b) oxidizing the partially-oxidized compounds formed in said first oxidation zone in a second oxidation zone in the presence of an additional amount of water up to a concentration of from about 20 to 70% by weight of the liquid phase and in the presence of an additional amount of a catalyst comprising a mixture of cobalt and manganese salts, at a temperature of from about 180° to 200° C. and a pressure high enough to maintain an oxygen partial pressure in said second zone of at least about 0.05 kg/cm$^2$, the residence time in said second oxidation zone being such that not more than about 50% by weight of the equilibrium mixture is comprised of terephthalic acid;

(c) stripping p-xylene vapors from said second oxidation zone;

(d) separating crystals of crude terephthalic acid from the effluent from said second oxidation zone from the soluble components of said effluent;

(e) countercurrently washing the separated crystals with fresh water to produce a slurry;

(f) recycling from about 80 to 98% of said soluble components to the second oxidation zone, and recycling from about 2 and 20% of said soluble components to the first oxidation zone to provide the latter with heavy metal catalyst;

(g) heating said slurry of crude terephthalic acid crystals to a temperature at least about 5° C. higher than necessary for dissolving the crude terephthalic acid and having the resulting solution saturated with terephthalic acid;

(h) cooling the resulting solution of crude terephthalic acid to a temperature not lower than about 185° C. sufficient to crystallize the terephthalic acid, whereby a slurry of purified terephthalic acid crystals is produced;

(i) separating the crystals of terephthalic acid from the slurry of purified terephthalic acid at a temperature not lower than the final temperature of crystallization in step (h);

(j) countercurrently washing the separated crystals of purified terephthalic acid with fresh water; and (k) recovering and recycling to the second oxidation zone the dissolved material present in the water solution used for said washing step (j).

2. A process according to claim 1, wherein the oxidation in the first oxidation zone is carried out at a temperature between about 140° and 160° C.

3. A process according to claim 1, wherein the oxidation in the first oxidation zone takes place in the presence of not more than about 5 weight % of water.

4. A process according to claim 3, wherein the concentration of catalyst in the first reaction zone is comprised between about 1 and 10 mmoles of metal compound per kg of liquid phase.

5. A process according to claim 1, wherein the water concentration in the second oxidation zone is comprised between about 35 and 55% by weight of the liquid phase.

6. A process according to claim 5, wherein the catalyst concentration in the second oxidation zone is comprised between about 5 and 30 mmoles of metal compound per kg of liquid phase.

7. A process according to claim 1, further comprising the step of recycling the p-xylene vapors stripped from the second oxidation zone to the first oxidation zone.

8. A process according to claim 1, wherein said crystal separation step (d) comprises gravitational separation in a first sedimentation column and said crystal separation step (i) comprises gravitational separation in a second sedimentation column.

9. A process according to claim 8, wherein said washing step (e) comprises introducing fresh water near the bottom of said first sedimentation column, and said washing step (j) comprises introducing fresh water near the bottom of said second sedimentation column.

* * * * *